(12) United States Patent
Horvath

(10) Patent No.: US 8,465,473 B2
(45) Date of Patent: Jun. 18, 2013

(54) SURGICAL FOOTSWITCH WITH MOVABLE SHROUD

(75) Inventor: Christopher Horvath, Irvine, CA (US)

(73) Assignee: Novartis AG, Basel (CH)

( * ) Notice: Subject to any disclaimer, the term of this patent is extended or adjusted under 35 U.S.C. 154(b) by 1745 days.

(21) Appl. No.: 11/692,590

(22) Filed: Mar. 28, 2007

(65) Prior Publication Data

US 2008/0243105 A1   Oct. 2, 2008

(51) Int. Cl.
*A61B 17/00* (2006.01)
*H01H 3/14* (2006.01)

(52) U.S. Cl.
USPC .............................. 606/1; 200/86.5; 307/119

(58) Field of Classification Search
USPC ................ 606/1; 200/86.5, 563; 74/561, 563
See application file for complete search history.

(56) References Cited

U.S. PATENT DOCUMENTS

| | | |
|---|---|---|
| 2,986,953 A | 6/1961 | De Armond et al. |
| 3,761,598 A | 9/1973 | Haile |
| 3,789,836 A | 2/1974 | Girten |
| 3,841,172 A | 10/1974 | Pilch |
| 3,930,431 A | 1/1976 | Magadini |
| 3,980,849 A | 9/1976 | Straihammer |
| 4,168,707 A | 9/1979 | Douvas et al. |
| 4,172,217 A | 10/1979 | Miller |
| 4,202,037 A | 5/1980 | Glaser et al. |
| 4,267,414 A | 5/1981 | Brueggeman |
| 4,274,411 A | 6/1981 | Dotson, Jr. |
| 4,337,939 A | 7/1982 | Hoyle et al. |
| 4,383,167 A | 5/1983 | Gmeinder et al. |
| 4,544,243 A | 10/1985 | Munnerlyn |
| 4,652,215 A | 3/1987 | Kuroyanagi et al. |
| 4,833,306 A | 5/1989 | Milbrett |
| 4,837,857 A | 6/1989 | Scheller et al. |
| 4,844,259 A | 7/1989 | Glowczewskie et al. |
| 4,870,964 A | 10/1989 | Bailey, Jr. et al. |
| 4,871,336 A | 10/1989 | Scheurer |
| 4,901,454 A | 2/1990 | Walkhoff |
| 4,907,589 A | 3/1990 | Cosman |
| 4,965,417 A | 10/1990 | Massie |
| 4,977,811 A | 12/1990 | Suzuki et al. |
| 4,983,901 A | 1/1991 | Lehmer |
| 5,028,802 A | 7/1991 | Webb et al. |
| 5,048,870 A | 9/1991 | Mangini et al. |
| 5,091,656 A | 2/1992 | Gahn |
| 5,094,226 A | 3/1992 | Medcalf et al. |

(Continued)

FOREIGN PATENT DOCUMENTS

| | | |
|---|---|---|
| DE | 39 03 401 A | 8/1990 |
| DE | 3917876 | 12/1990 |

(Continued)

OTHER PUBLICATIONS

International Search Report and Written Opinion for PCT/US2006/25336, Publication No. WO2007/005507, dated Jan. 26, 2007, 8 pages.

(Continued)

*Primary Examiner* — Melanie Hand
(74) *Attorney, Agent, or Firm* — Darien Reddick

(57) ABSTRACT

The present invention provides a surgical footswitch with a movable shroud. The footswitch is capable of controlling different kinds of surgical instruments and is adaptable by moving the shroud to meet the convenience and safety requirements of each kind of surgical instrument.

21 Claims, 5 Drawing Sheets

U.S. PATENT DOCUMENTS

| | | | |
|---|---|---|---|
| 5,157,603 | A | 10/1992 | Scheller et al. |
| 5,180,925 | A | 1/1993 | Lieb |
| 5,206,672 | A | 4/1993 | Rowe |
| 5,237,891 | A | 8/1993 | Lundberg et al. |
| 5,268,624 | A | 12/1993 | Zanger |
| 5,283,943 | A | 2/1994 | Aguayo et al. |
| 5,303,085 | A | 4/1994 | Rallison |
| 5,308,355 | A | 5/1994 | Dybbs |
| 5,324,900 | A | 6/1994 | Gonser et al. |
| 5,342,293 | A | 8/1994 | Zanger |
| 5,403,276 | A | 4/1995 | Schechter et al. |
| 5,408,076 | A | 4/1995 | Griffanti |
| 5,422,521 | A | 6/1995 | Neer et al. |
| 5,423,231 | A | 6/1995 | Helfrich et al. |
| 5,450,143 | A | 9/1995 | Rowe et al. |
| 5,455,766 | A | 10/1995 | Scheller et al. |
| 5,488,223 | A | 1/1996 | Austin et al. |
| 5,535,642 | A | 7/1996 | Moll |
| 5,545,160 | A | 8/1996 | O'Rourke |
| 5,549,597 | A | 8/1996 | Shimmick et al. |
| 5,554,894 | A | 9/1996 | Sepielli |
| 5,580,347 | A | 12/1996 | Reimels |
| 5,619,377 | A | 4/1997 | Rallison |
| 5,635,777 | A | 6/1997 | Telymonde et al. |
| 5,642,227 | A | 6/1997 | Rallison |
| 5,662,006 | A | 9/1997 | Angeltun |
| 5,673,151 | A | 9/1997 | Rallison |
| 5,674,233 | A | 10/1997 | Dybbs |
| 5,724,244 | A | 3/1998 | Yabuki |
| 5,787,760 | A | 8/1998 | Thorlakson |
| 5,810,765 | A | 9/1998 | Oda |
| 5,825,982 | A | 10/1998 | Wright et al. |
| 5,842,173 | A | 11/1998 | Strum et al. |
| 5,845,264 | A | 12/1998 | Nellhaus |
| 5,899,674 | A | 5/1999 | Jung et al. |
| 5,910,110 | A | 6/1999 | Bastable |
| 5,969,791 | A | 10/1999 | Rowe |
| 5,983,749 | A | 11/1999 | Holtorf |
| 5,990,400 | A | 11/1999 | Hoshino |
| 5,991,087 | A | 11/1999 | Rallison |
| 5,996,889 | A | 12/1999 | Fuchs et al. |
| 5,997,528 | A | 12/1999 | Bisch et al. |
| 6,005,482 | A | 12/1999 | Moran et al. |
| 6,010,496 | A | 1/2000 | Appelbaum et al. |
| 6,030,290 | A | 2/2000 | Powell et al. |
| 6,036,458 | A | 3/2000 | Cole et al. |
| 6,039,565 | A | 3/2000 | Chou et al. |
| 6,055,458 | A | 4/2000 | Cochran et al. |
| 6,059,544 | A | 5/2000 | Jung et al. |
| 6,066,129 | A | 5/2000 | Larson |
| 6,078,681 | A | 6/2000 | Silver |
| 6,087,941 | A | 7/2000 | Ferraz |
| 6,098,892 | A | 8/2000 | Peoples, Jr. |
| 6,099,521 | A | 8/2000 | Shadduck |
| 6,106,512 | A | 8/2000 | Cochran et al. |
| 6,117,126 | A | 9/2000 | Appelbaum et al. |
| 6,149,621 | A | 11/2000 | Makihara |
| 6,149,643 | A | 11/2000 | Herekar et al. |
| 6,150,623 | A | 11/2000 | Chen |
| 6,155,975 | A | 12/2000 | Urich et al. |
| 6,159,205 | A | 12/2000 | Herekar et al. |
| 6,179,829 | B1 | 1/2001 | Bisch et al. |
| 6,193,710 | B1 | 2/2001 | Lemberg |
| 6,204,491 | B1 | 3/2001 | Montani |
| 6,238,623 | B1 | 5/2001 | Amhof et al. |
| 6,251,113 | B1 | 6/2001 | Appelbaum et al. |
| 6,341,726 | B1 | 1/2002 | Castanedo et al. |
| 6,360,630 | B2 | 3/2002 | Holtorf |
| 6,394,999 | B1 | 5/2002 | Williams et al. |
| 6,452,120 | B1 | 9/2002 | Chen |
| 6,452,123 | B1 | 9/2002 | Chen |
| 6,485,413 | B1 | 11/2002 | Boppart et al. |
| 6,491,686 | B2 | 12/2002 | Lemberg |
| 6,506,050 | B1 | 1/2003 | Steddin |
| 6,512,530 | B1 | 1/2003 | Rzepkowski et al. |
| 6,514,268 | B2 | 2/2003 | Finlay et al. |
| 6,536,300 | B1 | 3/2003 | Gonring |
| 6,583,796 | B2 | 6/2003 | Jamar et al. |
| D478,323 | S | 8/2003 | Peterson et al. |
| 6,602,185 | B1 | 8/2003 | Uchikubo |
| 6,623,429 | B2 | 9/2003 | Percival et al. |
| 6,639,332 | B2 | 10/2003 | Metzler et al. |
| 6,641,039 | B2 | 11/2003 | Southard |
| 6,648,223 | B2 | 11/2003 | Boukhny et al. |
| 6,659,998 | B2 | 12/2003 | DeHoogh et al. |
| 6,669,340 | B2 | 12/2003 | Percival et al. |
| 6,671,535 | B1 | 12/2003 | McNichols et al. |
| 6,674,030 | B2 | 1/2004 | Chen et al. |
| 6,689,975 | B2 | 2/2004 | Metzler et al. |
| 6,726,625 | B2 | 4/2004 | Luce |
| 6,742,286 | B2 | 6/2004 | Giovale |
| 6,743,245 | B2 | 6/2004 | Lobdell |
| 6,749,302 | B2 | 6/2004 | Percival et al. |
| 6,751,473 | B1 | 6/2004 | Goyal et al. |
| 6,783,523 | B2 | 8/2004 | Qin et al. |
| 6,784,388 | B1 | 8/2004 | Braaten |
| 6,786,502 | B2 | 9/2004 | Carlson |
| 6,816,316 | B2 | 11/2004 | Caudle et al. |
| 6,862,951 | B2 | 3/2005 | Peterson et al. |
| 6,893,261 | B1 | 5/2005 | Feine |
| 6,908,196 | B2 | 6/2005 | Herekar et al. |
| 6,945,650 | B2 | 9/2005 | Beverly |
| 6,962,094 | B2 | 11/2005 | Porter et al. |
| 6,962,581 | B2 | 11/2005 | Thoe |
| 7,001,018 | B1 | 2/2006 | Martin |
| 7,012,203 | B2 | 3/2006 | Hanson et al. |
| 7,019,234 | B1 | 3/2006 | Mezhinsky et al. |
| 7,084,364 | B2 | 8/2006 | Mezhinsky |
| 7,185,555 | B2 | 3/2007 | Peterson et al. |
| 7,193,169 | B2 | 3/2007 | Mezhinsky et al. |
| 7,259,340 | B2 | 8/2007 | Blaha et al. |
| 7,323,646 | B2 | 1/2008 | Braaten |
| 7,381,917 | B2 | 6/2008 | Dacquay et al. |
| 7,400,752 | B2 | 7/2008 | Zacharias |
| 7,422,432 | B2 | 9/2008 | Warner |
| 7,422,582 | B2 | 9/2008 | Malackowski et al. |
| 7,439,463 | B2 | 10/2008 | Brenner et al. |
| 7,476,799 | B2 | 1/2009 | Purchon et al. |
| 7,568,619 | B2 | 8/2009 | Todd et al. |
| 7,619,171 | B2 | 11/2009 | Horvath et al. |
| 7,708,404 | B2 | 5/2010 | Gaida et al. |
| 2001/0006818 | A1 | 7/2001 | Amhof et al. |
| 2001/0020401 | A1 | 9/2001 | Holtorf |
| 2002/0045887 | A1 | 4/2002 | Todd |
| 2002/0047990 | A1 | 4/2002 | Fergason et al. |
| 2002/0115917 | A1 | 8/2002 | Honda et al. |
| 2003/0047434 | A1 | 3/2003 | Hanson et al. |
| 2003/0073980 | A1 | 4/2003 | Finlay et al. |
| 2003/0111327 | A1 | 6/2003 | Metzler et al. |
| 2003/0132092 | A1 | 7/2003 | Metzler et al. |
| 2003/0213333 | A1 | 11/2003 | McVicar |
| 2004/0024384 | A1 | 2/2004 | Novak |
| 2004/0030367 | A1 | 2/2004 | Yamaki et al. |
| 2004/0102799 | A1 | 5/2004 | Perez et al. |
| 2004/0106915 | A1 | 6/2004 | Thoe |
| 2004/0115591 | A1 | 6/2004 | Warner |
| 2005/0277913 | A1 | 12/2005 | McCary |
| 2006/0043179 | A1 | 3/2006 | Nycz et al. |
| 2006/0114175 | A1 | 6/2006 | Boukhny |
| 2006/0116667 | A1 | 6/2006 | Hamel et al. |
| 2006/0145540 | A1 | 7/2006 | Mezhinsky |
| 2006/0149418 | A1 | 7/2006 | Anvari |
| 2006/0219049 | A1* | 10/2006 | Horvath et al. ................. 74/560 |
| 2006/0236242 | A1 | 10/2006 | Boukhny et al. |
| 2006/0247659 | A1 | 11/2006 | Moeller et al. |
| 2006/0270913 | A1 | 11/2006 | Todd |
| 2007/0008624 | A1 | 1/2007 | Hirayama |
| 2007/0081078 | A1 | 4/2007 | Cummings |
| 2007/0135866 | A1 | 6/2007 | Baker et al. |
| 2007/0146130 | A1 | 6/2007 | Hannemann et al. |
| 2007/0152508 | A1 | 7/2007 | Mezhinsky |
| 2008/0060662 | A1 | 3/2008 | Oh et al. |
| 2008/0085499 | A1 | 4/2008 | Horvath |
| 2008/0086117 | A1 | 4/2008 | Cao |
| 2008/0089277 | A1 | 4/2008 | Alexander et al. |
| 2008/0140158 | A1 | 6/2008 | Hamel et al. |
| 2008/0161783 | A1 | 7/2008 | Cao |

| | | | |
|---|---|---|---|
| 2008/0243105 A1 | 10/2008 | Horvath | |
| 2008/0243142 A1 | 10/2008 | Gildenberg | |
| 2008/0281301 A1 | 11/2008 | Deboer et al. | |
| 2009/0049397 A1 | 2/2009 | Boukhny | |
| 2009/0121865 A1 | 5/2009 | Hamel et al. | |
| 2009/0125337 A1 | 5/2009 | Abri | |
| 2009/0300507 A1 | 12/2009 | Raghavan et al. | |
| 2009/0303315 A1 | 12/2009 | Charlesworth | |

FOREIGN PATENT DOCUMENTS

| | | |
|---|---|---|
| DE | 19509680 | 9/1996 |
| DE | 20100591 | 6/2001 |
| DE | 20105851 | 10/2001 |
| DE | 10033680 | 1/2002 |
| DE | 10104162 | 8/2002 |
| DE | 10245591 | 4/2005 |
| DE | 102005010094 | 9/2006 |
| EP | 0550124 | 7/1993 |
| EP | 0630820 | 12/1994 |
| EP | 0656612 A1 | 6/1995 |
| EP | 0789929 | 7/2002 |
| EP | 1394828 | 3/2004 |
| EP | 1498082 | 1/2005 |
| EP | 1714617 | 10/2006 |
| FR | 2646545 | 11/1990 |
| GB | 1 051 785 | 12/1966 |
| GB | 1063067 | 3/1967 |
| JP | 56-012464 | 7/1954 |
| JP | 6-142105 | 5/1994 |
| JP | 07-103130 | 4/1995 |
| JP | 09-205291 A | 8/1997 |
| JP | 2000 217836 | 8/2000 |
| JP | 2000-229102 | 8/2000 |
| JP | 2003-314437 | 11/2003 |
| JP | 2004-030563 | 4/2004 |
| JP | 2004-537367 | 12/2004 |
| WO | WO 96/13845 | 5/1996 |
| WO | WO 98/08442 | 3/1998 |
| WO | WO 99/017818 | 10/1998 |
| WO | WO 99/14648 | 3/1999 |
| WO | WO 00/12037 | 3/2000 |
| WO | WO 0186369 | 11/2001 |
| WO | WO 02/01310 | 1/2002 |
| WO | WO 02/32354 | 4/2002 |
| WO | WO 03/053293 | 7/2003 |
| WO | WO 03/053294 | 7/2003 |
| WO | WO 2004/019751 | 3/2004 |
| WO | WO 2005/084570 | 9/2005 |
| WO | WO 2006/026289 | 3/2006 |
| WO | WO 2006/060423 | 6/2006 |
| WO | WO 2007/005507 | 1/2007 |
| WO | WO 2008/131362 | 10/2008 |
| WO | WO 2009/023408 | 2/2009 |

OTHER PUBLICATIONS

Search Report of R.O.C. for Application No. 095123616, Filing Date Jun. 29, 2006, Completed Dec. 20, 2011.
European Search Report for Application No. 06785823.3, Publication No. EP1897105, Published Mar. 12, 2008, dated Jun. 5, 2009, 4 pages.
Partial European Search Report for Application No. 06111409.6, Publication No. EP1714617, Dated Jul. 5, 2006, Published Oct. 25, 2006, 5 pages.
Extended European Search Report for Application No. 06111409.6, Publication No. EP1714617, Dated Sep. 8, 2006, Published Oct. 25, 2006, 14 pages.
Written Opinion of the International Searching Authority, International Application No. PCT/US08/70715, dated Feb. 15, 2010, 5 pages.
International Search Report for PCT/US2003/04310, Publication No. WO03081379, dated Sep. 23, 2003, 1 page.
International Search Report for PCT/US2009/046229, Publication No. WO2009/149244, dated Jan. 19, 2010, 6 pages.

* cited by examiner

SURGICAL FOOTSWITCH WITH MOVABLE SHROUD

FIELD OF THE INVENTION

The present invention relates generally to systems and methods for controlling a surgical system, and more particularly, to a surgical footswitch with a movable shroud.

BACKGROUND

During the use of a complex patient treatment apparatus or surgical system, for example, surgical equipment used when performing ophthalmic surgery, the control of a variety of different subsystems, such as pneumatic and electronically driven subsystems, may be required. Typically, the operation of the subsystems is controlled by a microprocessor-driven console. The microprocessor controls within a surgical console receive mechanical inputs from either the operator of the surgical system or from an assistant to govern the operation of a subsystem within the patient treatment apparatus. Control input devices may include switches on the console, remote hand switches, remote footswitches, and other control input devices. In a footswitch, the mechanical inputs originate from the movement of the foot of an operator. The mechanical inputs from the movement of the foot of the operator are translated into electrical signals that are fed to the microprocessor controls. Typical foot switches include a foot pedal similar to an accelerator pedal in an automobile. Some footswitch assemblies also include side or wing switches mounted to housings on either side of the foot pedal in order to provide additional capabilities to the footswitch.

Actuation of the various control input devices in the system may be used, for example, to regulate vacuum, rotational speed, output power, reciprocal motion, and on/off state of one or more surgical instruments. In many surgical procedures it is necessary to switch from one type of surgical instrument to another, for example, from a rotary handpiece or suction aspirator to a laser coagulator. Typically, a different footswitch is provided for each surgical console or instrument. With multiple surgical instruments in use during a procedure, the operation environment can become cluttered with control devices. Furthermore, different types of instruments may have different convenience and safety requirements. For example, standards for surgical lasers require that a footswitch used to control a laser include a shroud to guard against accidental laser activation. However, there is no requirement for such a shroud, for example, for footswitch activated rotary handpieces and suction aspirators and the use of a shroud in these applications may be undesirable.

SUMMARY

The present invention provides a surgical footswitch with a movable shroud. The footswitch is capable of controlling different kinds of surgical instruments and is adaptable, by moving the shroud, to meet the convenience and safety requirements of each kind of surgical instrument.

In one aspect of the invention, the surgical footswitch includes a base and a foot operated input device mounted to the base to activate a surgical instrument. A shroud is movable between a first position in which the shroud blocks access to the input device from at least a first direction and a second position in which the shroud permits access to the input device from the first direction.

In another aspect of the invention, the footswitch includes an interlock preventing the footswitch from activating the instrument unless the shroud is in the first position.

In another aspect of the invention, the footswitch includes a drive unit operable to move the shroud.

In another aspect of the invention, a surgical system includes a surgical instrument, a surgical console connected the instrument, and a surgical footswitch connected to the console. A shroud is movable from a first position in which the shroud blocks access to a portion of the footswitch from at least a first direction and a second position in which the shroud permits access from the first direction.

In another aspect of the invention, the console detects whether the shroud is in the first position before enabling the footswitch to control the instrument.

In another aspect of the invention, the console is operable to cause a drive unit to move the shroud.

In another aspect of the invention, the console is responsive to a mode selector to select between two surgical instruments and to cause the drive unit to move the shroud to a position corresponding to the selected instrument.

One embodiment of the present invention comprises a method of using a surgical footswitch operably connecting the footswitch to a first surgical instrument; detecting whether a shroud is in a first position relative to the footswitch in which first position the shroud blocks access to a portion of the input device from at least a first direction; enabling the footswitch to activate the first surgical instrument only if the shroud is in the first position.

In another aspect of the invention, the method includes activating a drive unit to move the shroud.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
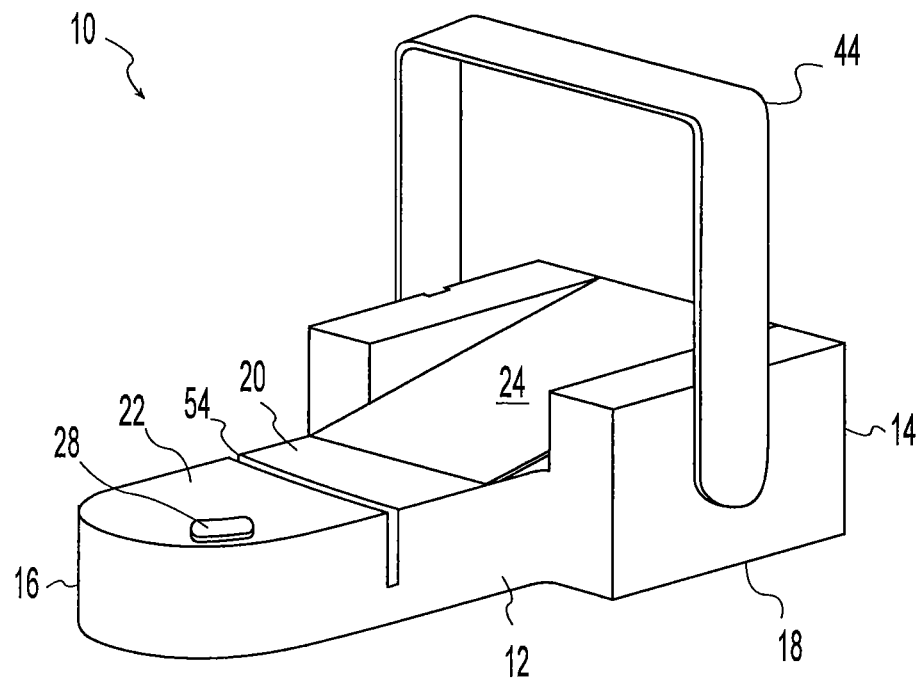
FIG. 1 is a perspective view of a surgical footswitch according to the present invention with a shroud in an upright engaged position.

Embodiments of a surgical footswitch with a movable shroud according to the present invention may include one or more foot operated input devices. Input devices may include dual state input devices, multiple state input devices with more than two states, and/or infinitely adjustable input devices. Input devices may include digital input devices and/or analogue input devices. For example, input devices may include switches with two or more poles, potentiometers, Hall Effect sensors, digital encoders, and/or any other suitable input devices. For example, the footswitch may include a linear potentiometer for speed control input and one or more switches for instrument activation.

The shroud may be movable from a first position in which the shroud is mounted to the footswitch and a second position in which the shroud is completely detached from the footswitch. For example the shroud may be releasably attached to the footswitch by frictional engagement, snap fit, bolting, clipping, hook and loop fastener, sprung engagement, ratchet engagement, and/or any other suitable engagement mechanism. For example, the shroud may removably clip onto the footswitch in one or more input device blocking positions.

The shroud may be movable from a first relative position mounted to the footswitch to a second relative position mounted to the footswitch. The shroud may be movable by pivoting, translating, rotating, sliding, telescoping, and/or any other suitable motion. For example, the shroud may be hinged to the footswitch to permit it being pivoted between the first and second positions.

The shroud may block access to one or more input devices from one or more directions. In one example, the shroud may project over a portion of the footswitch. For example, the shroud may include a band of material that projects over a portion of the footswitch. In another example, the shroud may block access to a portion of the footswitch from the sides and top. For example, a band of material may project upwardly from a side of the footswitch and extend over the top of a portion of the footswitch. In another example, the shroud may enclose a portion of the footswitch. For example, the shroud may form a box covering a portion of the footswitch and being open at one side to allow entry of the user's foot. The shroud may function as a handle for carrying and/or repositioning the footswitch.

The shroud may be manually positioned by a user in the first and second positions, manually positioned in one position and machine driven into the second position, or machine driven between the first and second positions. The shroud may be machine driven by a spring, motor, servo, solenoid, gear drive, and/or any other suitable mechanism. For example, the shroud may be manually moved against spring tension to move the shroud into a first position in which it is held by a solenoid and automatically moved to the second position by the surgical system moving the solenoid and allowing the spring to drive the shroud to the second position. In another example, the surgical system may actuate a motor to drive the shroud between the first and second positions based on surgical mode selection.

The shroud and footswitch may define an interlock that disables one or more surgical instrument operational modes if the shroud is not properly positioned. The interlock may function to disable one or more footswitch input devices when the shroud is not in a desired position. For example, the shroud may complete an electrical circuit enabling an input device when the shroud is properly positioned. The interlock may function as a switch to directly enable and disable surgical instrument modes. The interlock may cooperate with a user operated mode switch to verify proper shroud positioning prior to enabling certain surgical instrument modes. The interlock may include a sensor to determine proper shroud positioning. The sensor may include pushbutton mechanical switches, reed switches, Hall Effect sensors, electrical contacts, optical sensors, and/or any other suitable sensor able to indicate the presence and/or proper position of the shroud. For example, a Hall Effect switch mounted to the footswitch may be positioned to sense the presence of the shroud.

A surgical console may include a microprocessor that compares the condition of footswitch input devices, interlock sensors, console switches, and/or other input devices to select and/or enable different instrument operation modes. The console may provide feedback to the user to indicate the shroud position. The feedback may confirm the presence or absence of the shroud and/or its proper positioning. The feedback may suggest a course of action that is required to enable a surgical instrument mode. For example, the console may provide feedback instructing the user to engage the shroud in a blocking position. The feedback may include audible feedback, visual feedback, tactile feedback, and/or any other suitable feedback able to be detected by the user. For example the feedback may include bells, buzzers, voice commands, lights, printed messages, vibrations, and/or other feedback.

The footswitch control inputs and the console control inputs can be setup to control instrument parameters such as vacuum, speed, output power, instrument arming and disarming, and instrument on and off cycling. Some of the control inputs can be setup to control one instrument while others control another instrument. In this way, both instruments can be used in quick succession with no changeover being required. Alternatively, one or more of the control inputs can be used to change the footswitch operation mode such that in one mode a control input controls one instrument and in another mode the control input controls another instrument.

The footswitch may communicate with a surgical instrument and/or surgical console through a wired or a wireless connection.

The footswitch of the present invention will be described in use to provide control input to a surgical console connected to both a powered vitrectomy handpiece and a laser coagulator in an ophthalmic procedure. These embodiments are for illustration only and it will be understood that the footswitch of the present invention may be suitable for controlling a wide range of surgical instruments directly and by way of a surgical console as well as for controlling surgical instruments in a wide range of surgical procedures performed on various portions of the anatomy.

Referring to FIGS. 1-5, an illustrative footswitch 10 includes a housing 12 having a front end 14, a back end 16, a bottom 18, and a top 20. The housing 12 defines a heel plate 22 on a portion of its top 20 near the back end 16. A treadle 24 overlies a portion of the top 20 near the front end 14. A user can place his foot on the top of the housing 12 with his heel in contact with the heel plate 22 and the ball of his foot on the treadle 24. Two input devices are provided in the form of a treadle switch 26 (FIG. 5) operable by pressing downwardly on the treadle 24 with the ball of the foot and a heel switch 28 operable by pressing downwardly with the heel. The footswitch 10 communicates with a surgical console 32 (FIG. 5) by way of a cable 34. In other embodiments, footswitch 10 can communicate with surgical console 32 by way of a wireless connection as will be known to those having ordinary skill in the art. The switches 26, 28 are activated to control surgical instruments linked to the console 32. The illustrative console 32 includes controls for a vitrectomy handpiece 36 and a laser coagulator 38. The console 32 further includes a control input in the form of a switch 40. Finally, the console 32 includes an indicator light 42 for providing feedback to a user. In the illustrative footswitch, the treadle switch 26 controls the vitrectomy handpiece 36 in a first mode and the laser coagulator 38 in a second mode. The heel switch 28 and console switch 40 may be used interchangeably to change modes from vitrectomy handpiece 36 control to laser 38 control.

Figure 2:
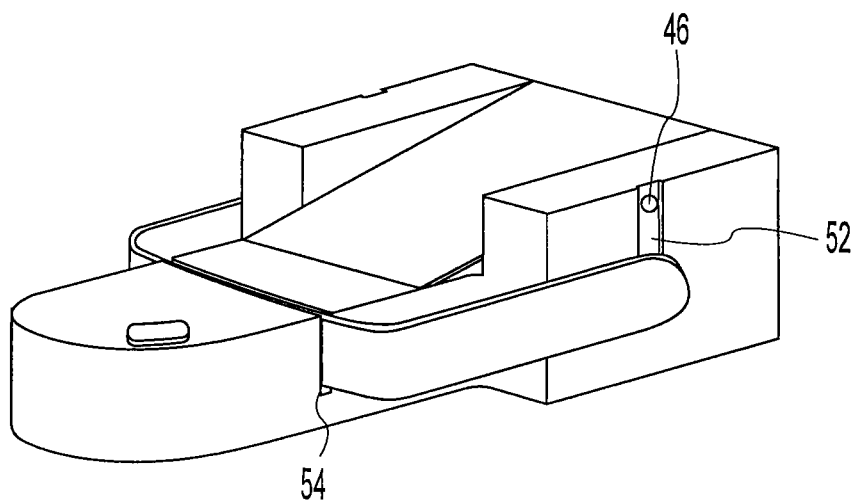
FIG. 2 is a perspective view of the footswitch of FIG. 1 with the shroud folded into a forward disengaged position.
Figure 3:
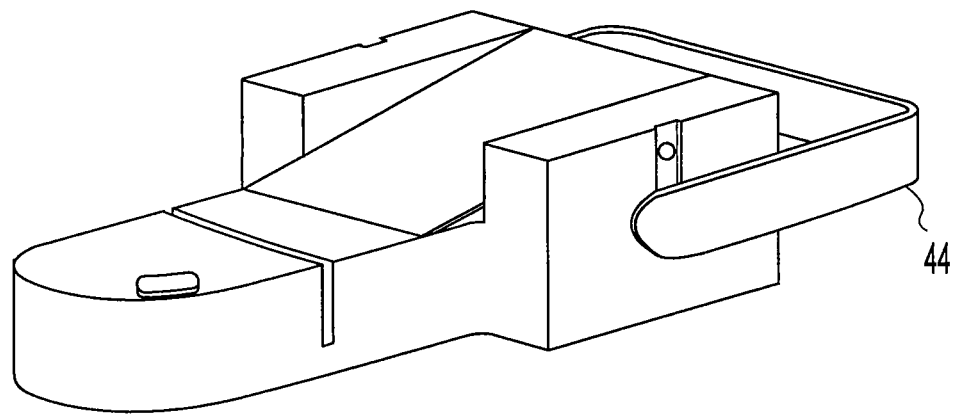
FIG. 3 is a perspective view of the footswitch of FIG. 1 with the shroud folded into a rearward disengaged position.
Figure 4:
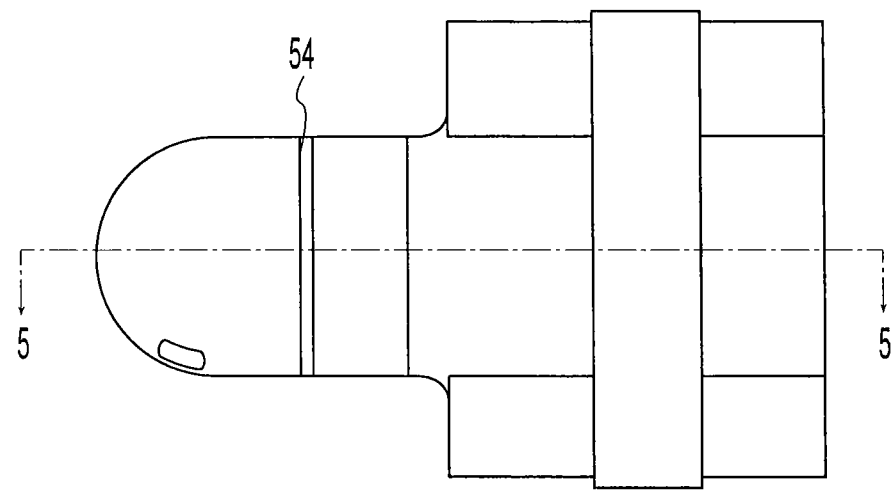
FIG. 4 is a top plan view of the footswitch of FIG. 1.
Figure 5:
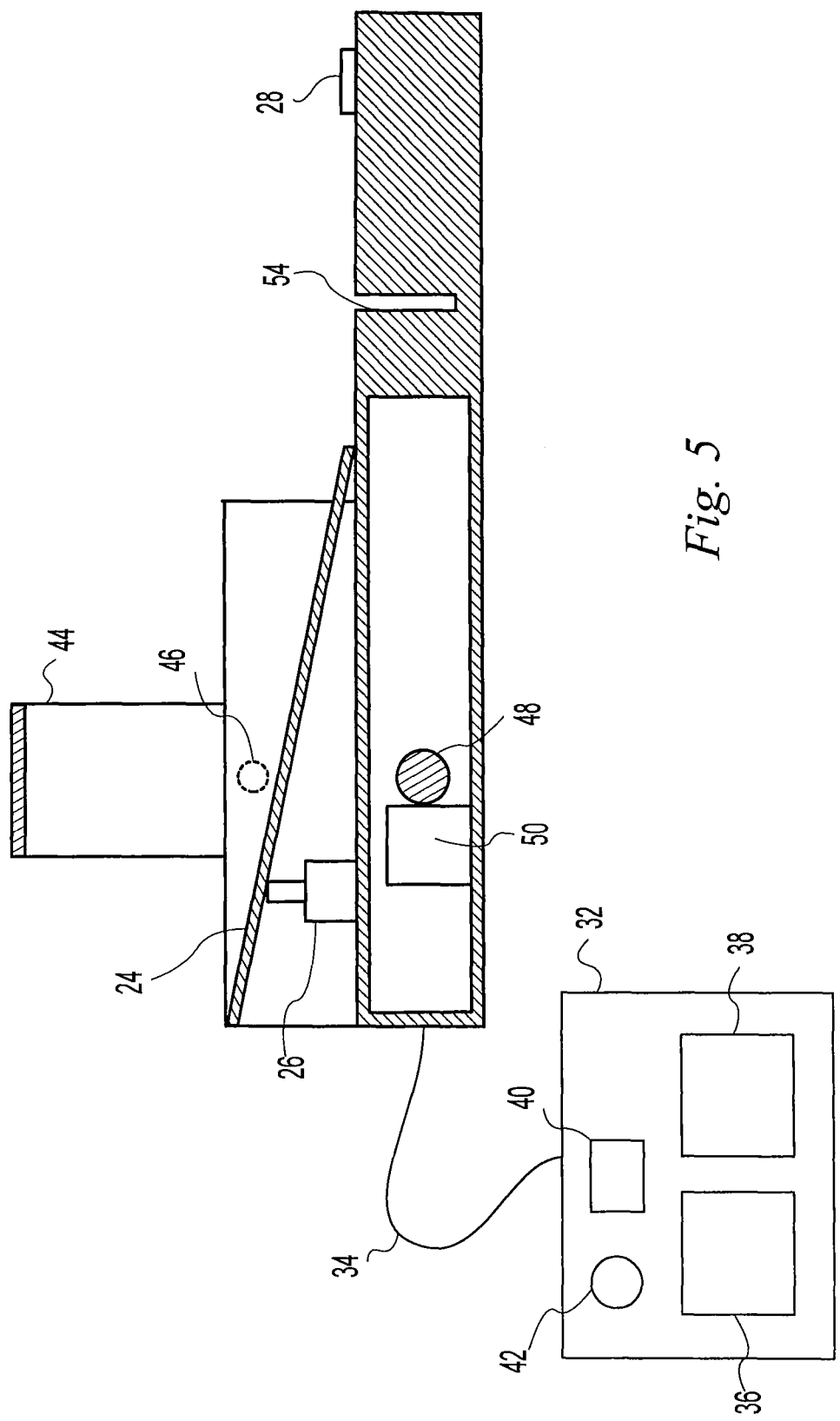
FIG. 5 is a simplified, schematic, cross section of the footswitch of FIG. 1 taken along line 5-5 of FIG. 4.

A shroud 44 is mounted to the housing 12 and is movable between an engaged position as shown in FIG. 1 and disengaged positions as shown in FIGS. 2 and 3. In the engaged position, the shroud 44 blocks inadvertent contact with the treadle 24 from the sides and top such as when the footswitch 10 is being repositioned on the floor. The footswitch includes a sensor 46 (FIG. 2) that senses if the shroud 44 is in the engaged position. The sensor forms part of an interlock that prevents the laser 38 from firing unless the shroud 44 is in the engaged position. The illustrative shroud 44 pivots about an axel 48 (FIG. 5) coupled to a drive unit 50. The drive unit 50 pivots the shroud 44 between the engaged and disengaged positions based on control signals received from the surgical console.

In an alternative embodiment, the shroud 44 is manually attached and detached from the housing 12 by a tongue and groove engagement of the shroud 44 with a groove 52 in the side of the housing 12.

FIG. 2 illustrates an arrangement in which the shroud 44 pivots forwardly to the disengaged position and is stowed in a slot 54 in the housing 12 between the heel plate 22 and the treadle 24. When the shroud 44 is stowed in this forward position, it and the housing form a compact assembly with few projections into the surgical suite. This arrangement also has the advantage of requiring the user to remove his foot from the treadle 24 when the shroud 44 is moved from the disengaged position to the engaged position. The user then must intentionally replace his foot under the shroud 44 to operate the treadle 24. This provides additional security against inadvertent instrument activation upon changing modes. A driven shroud 44, like that in the illustrative embodiment, will tend to force a users foot up and away from the treadle 24 as it moves to the engaged position. However, the drive unit 50 may include a clutch or other device that prevents the shroud from moving if it contacts an object such as the user's foot while moving to the engaged or disengaged position.

FIG. 3 illustrates an arrangement in which the shroud 44 pivots forwardly to the disengaged position such that it projects from the front of the housing and functions as a carrying handle. The shroud 44 may also be used as a handle in the engaged position of FIG. 1. The shroud 44 may be configured to be selectively movable to both the forward and rearward disengaged positions.

Figure 6:
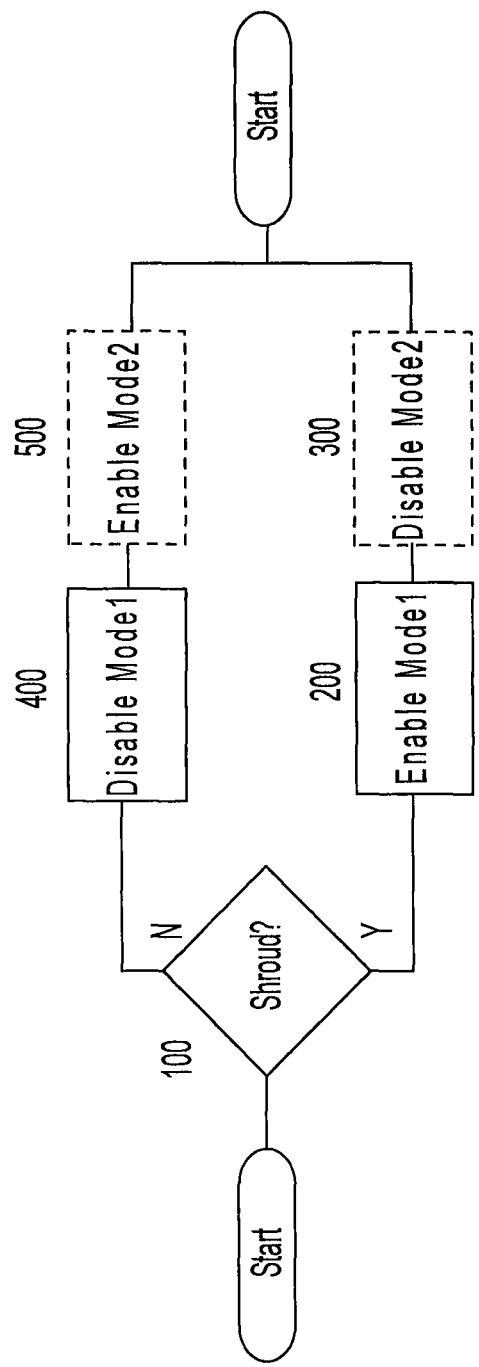
FIG. 6 is a logic flow diagram illustrating a method of controlling surgical equipment with the footswitch of FIG. 1.

FIG. 6 depicts a logic flow diagram illustrating an example of a method of controlling surgical equipment with the footswitch 10. In the illustrative embodiment, Mode 1 corresponds to laser 38 control and Mode 2 corresponds to vitrectomy handpiece 36 control. A microprocessor in the console 32 reads the condition of the system input devices to establish the system mode of operation and to prevent laser 38 use without the shroud 44 in place. The console checks the condition of the sensor 46 in step 100 to determine if the shroud 44 is in the engaged position. If it is, then the console enables the laser and puts it under control of the footswitch in step 200. The illustrative system also disables the handpiece control in step 300. If the shroud 44 is not in the engaged position, then the console disables the laser in step 400. The illustrative system also enables the handpiece control in step 500. In a system in which the footswitch has input devices to simultaneously control both Mode 1 and Mode 2, steps 300 and 500 may be omitted if it is desired to make only Mode 1 dependent on the status of the shroud 44 engagement.

Figure 7:
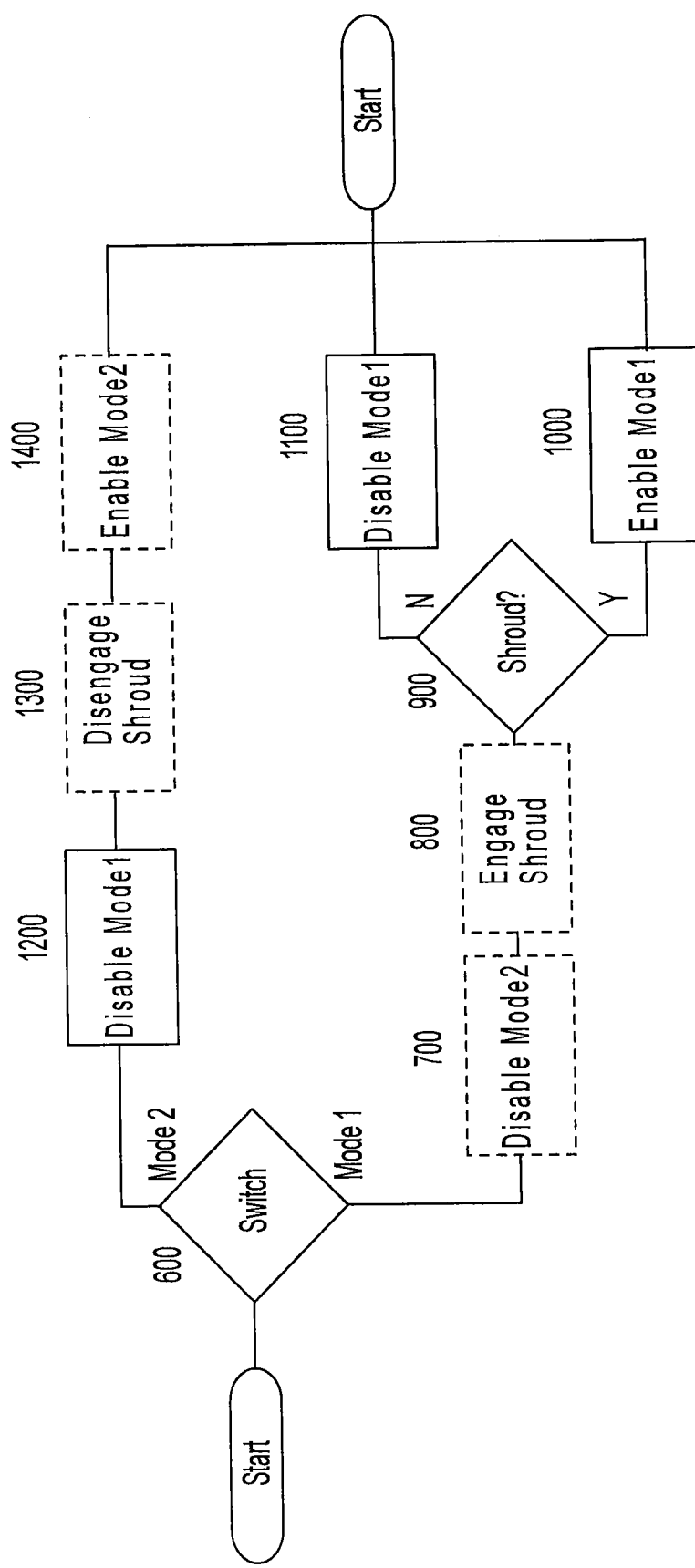
FIG. 7 is a logic flow diagram illustrating a method of controlling surgical equipment with the footswitch of FIG. 1.

FIG. 7 depicts a logic flow diagram illustrating an example of a more detailed method of controlling surgical equipment with the footswitch 10. Again, Mode 1 corresponds to laser 38 control and Mode 2 corresponds to vitrectomy handpiece 36 control. When a mode change is requested, such as by depressing the console switch 40 or the heel switch 28, the console determines which mode has been requested in step 600. If Mode 1 has been requested, Mode 2 is disabled in step 700 and the drive unit is signaled to engage the shroud in step 800. The interlock system performs a safety check in step 900. If the shroud 44 is engaged, Mode 1 is enabled in step 1000. If the shroud is not engaged, Mode 1 is disabled in step 1100 and the laser 38, in this example, is locked out until the shroud 44 is engaged.

If Mode 2 has been requested, Mode 1 is disabled in step 1200 and the drive unit is signaled to disengage the shroud 44 in step 1300. Mode 2 is enabled in step 1400. If it is only desired to have Mode 1 dependent on shroud 44 placement, steps 700 and 1400 are optional. While the illustrative footswitch includes a drive unit for driving the shroud 44 both to engage and disengage it, either one or both of steps 800 and 1300 may also represent manual shroud 44 positioning.

In either of the exemplary methods, the console 32 may also provide feedback indicating the position of the shroud 44 such as by illuminating the console light 42.

Although examples of a surgical footswitch with a movable shroud and its use have been described and illustrated in detail, it is to be understood that the same is intended by way of illustration and example only and is not to be taken by way of limitation. The invention has been illustrated in use with a surgical console to alternatively control a vitrectomy handpiece and a laser coagulator. However, the invention may control a single instrument directly or through a console, control multiple instruments alternatively, and/or control multiple instruments simultaneously. Likewise, the invention may be used to control any kind of surgical instrument for which footswitch control is appropriate. Also, particular physical attributes of the invention have been illustrated in the illustrative examples. However, these are intended as examples only. Accordingly, variations in and modifications to the surgical footswitch with a movable shroud and its use will be apparent to those of ordinary skill in the art, and the following claims are intended to cover all such modifications and equivalents.

What is claimed is:

1. A surgical footswitch for controlling a surgical instrument, the surgical footswitch comprising:
   a base;
   a foot operated input device mounted to the base and operable to activate the surgical instrument; and
   a shroud movable between a first position in which the shroud blocks access to the input device from at least a first direction and a second position in which the shroud permits access to the input device from the first direction.

2. The surgical footswitch of claim 1 further comprising an interlock operable to prevent the input device from activating the surgical instrument unless the shroud is in the first position.

3. The surgical footswitch of claim 2 in which the second position comprises removal of the shroud from the base.

4. The surgical footswitch of claim 2 in which the second position comprises a second position on the base.

5. The surgical footswitch of claim 4 in which the shroud is pivotably connected to the base and the shroud is pivotable between the first and second positions.

6. The surgical footswitch of claim 1 further comprising a drive unit mounted to the base, the drive unit being operable to move the shroud in at least one direction between the first and second positions.

7. The surgical footswitch of claim 6 in which the shroud is manually movable in at least one direction between the first and second positions.

8. The surgical footswitch of claim 6 in which the drive unit is operable to move the shroud in both directions between the first and second positions.

9. The surgical footswitch of claim 1 in which the shroud, in the second position, extends away from the base to define a carrying handle for the foot switch.

10. A surgical system comprising:
a first surgical instrument;
a surgical console operably connected to the first surgical instrument; and
a surgical footswitch operably connected to the surgical console, the footswitch having a foot operated input device operable to activate the surgical instrument, and a shroud movable from a first position in which the shroud blocks access to the input device from at least a first direction and a second position in which the shroud permits access to the input device from the first direction.

11. The surgical system of claim 10 wherein the footswitch includes a sensor operably connected to the surgical console, the sensor indicating to the console whether the shroud is in the first position, the console being operable to prevent the footswitch from activating the first surgical instrument when the shroud is not in the first position.

12. The surgical system of claim 10 further comprising a drive unit operably connected to the shroud to move the shroud between the first and second positions, the surgical console being operable to cause the drive unit to move the shroud.

13. The surgical system of claim 10 further comprising a mode selector operable to select between a first operational mode and a second operational mode, the surgical console being responsive to the mode selector to cause the drive unit to move the shroud.

14. The surgical system of claim 13 wherein the surgical console is further responsive to the mode selector to change the function of the footswitch input device.

15. The surgical system of claim 13 further comprising a second surgical instrument, the surgical console being responsive to the mode selector to select between the first and second surgical instruments, the surgical console being operable to cause the drive unit to move the shroud to the first position when the first instrument is selected.

16. The surgical system of claim 15 wherein the surgical console is operable to cause the drive unit to more the shroud to the second position when the second instrument is selected.

17. The surgical system of claim 13 wherein the first surgical instrument comprises a surgical laser.

18. A method of using a surgical footswitch comprising;
operably connecting the footswitch to a first surgical instrument, the footswitch comprising an input device and a shroud;
detecting whether the shroud is in a first position relative to the footswitch in which first position the shroud blocks access to a portion of the input device from at least a first direction;
enabling the footswitch to activate the first surgical instrument only if the shroud is in the first position.

19. The method of claim 18 further comprising:
activating a drive unit to move the shroud relative to the footswitch.

20. The method of claim 19 further comprising:
detecting a mode selector to select between first and second surgical modes; and
activating the drive unit to move the shroud between the first position and a second corresponding to the first and second surgical modes, the second shroud position permitting access to the input device from the first direction.

21. The method of claim 19 further comprising:
operably connecting the footswitch to a second surgical instrument;
detecting as mode selector to select between the first and second surgical instruments;
activating the drive unit to move the shroud to the first position when the first instrument is selected.

* * * * *